(12) United States Patent
Chen et al.

(10) Patent No.: US 11,110,143 B2
(45) Date of Patent: Sep. 7, 2021

(54) METHOD FOR PREPARING CITRUS-DERIVED COMPLEX PREBIOTIC AGENT AND USE OF THE SAME

(71) Applicant: ZHEJIANG UNIVERSITY, Hangzhou (CN)

(72) Inventors: Shiguo Chen, Hangzhou (CN); Jiaqi Zheng, Hangzhou (CN); Xingqian Ye, Hangzhou (CN); Donghong Liu, Hangzhou (CN); Hua Zhang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/754,137

(22) PCT Filed: Sep. 27, 2018

(86) PCT No.: PCT/CN2018/107919
§ 371 (c)(1),
(2) Date: Apr. 7, 2020

(87) PCT Pub. No.: WO2020/061891
PCT Pub. Date: Apr. 2, 2020

(65) Prior Publication Data
US 2021/0113645 A1    Apr. 22, 2021

(51) Int. Cl.
| | | |
|---|---|---|
| *A61K 36/00* | (2006.01) | |
| *A61K 36/752* | (2006.01) | |
| *A23L 33/00* | (2016.01) | |
| *A23L 33/105* | (2016.01) | |
| *A23L 33/135* | (2016.01) | |
| *A61K 9/08* | (2006.01) | |
| *A61K 9/14* | (2006.01) | |

(52) U.S. Cl.
CPC .......... *A61K 36/752* (2013.01); *A23L 33/105* (2016.08); *A23L 33/135* (2016.08); *A23L 33/30* (2016.08); *A61K 9/08* (2013.01); *A61K 9/14* (2013.01); *A61K 2236/331* (2013.01)

(58) Field of Classification Search
CPC ...................................................... A61K 36/00
USPC ....................................................... 424/725
See application file for complete search history.

(56) References Cited

FOREIGN PATENT DOCUMENTS

| CN | 101919522 Y | 12/2010 |
|---|---|---|
| CN | 103122038 Y | 5/2013 |
| CN | 106188335 A | 12/2016 |

OTHER PUBLICATIONS

International Search Report (PCT/CN2018/107919); dated May 23, 2019.

*Primary Examiner* — Michael V Meller
(74) *Attorney, Agent, or Firm* — W&G Law Group LLP

(57) ABSTRACT

The present disclosure discloses a method for preparing a citrus-derived complex prebiotic agent. The method comprises the following steps: removing external citrus peels after blanching citrus fruits with hot water, soaking citrus segments after splitting with an acid solution and an alkali solution to remove membranes of the citrus segments, and adjusting the pH of the obtained alkali soaking water with acid soaking water or acid to be weakly acidic or neutral to obtain the complex prebiotic agent, which has the function of reversing intestinal flora disorders. Compared with the traditional prebiotic product preparing method, the product prepared by the method contains prebiotic functional components with different targets such as pectin, flavonoids, oligosaccharides, and other fibers at the same time, and has the efficacies of regulating intestinal flora and reversing intestinal flora disorders caused by antibiotics. At the same time, the preparing method has the characteristics of simple operation and low cost, perfectly supplements a comprehensive utilization process of citrus fruit processing, solves the discharge problem of citrus fruit processing water, and generates very good social benefits.

5 Claims, 2 Drawing Sheets

METHOD FOR PREPARING CITRUS-DERIVED COMPLEX PREBIOTIC AGENT AND USE OF THE SAME

TECHNICAL FIELD

The present disclosure belongs to the field of comprehensive utilization of canned fruit and vegetable production wastewater, and particularly relates to a method for preparing a citrus-derived complex prebiotic agent and a use of the same.

BACKGROUND

The citrus fruit has a large production and a wide planting area, and is one of the most important cash crops and international agricultural products and processed goods. China's citrus fruit production ranks among the best in the world all the year round, and most of them are Citrus reticulate Blanco and grapefruit. The abundant raw material sources make China become a major country for citrus fruit processing, especially canned citrus fruit segments in syrup. Due to the unique citrus varieties and relatively cheap labor in China, China's canned citrus fruit products have unique advantages in the world, accounting for 70-80% of the total international market share, and increasing year by year. During the processing of canned citrus fruits, citrus fruit segment membranes must be removed, and the segment membranes are removed by subjecting the citrus fruit segments to acid water treatment and alkaline water treatment during production. During the treatments, discharged water dissolved with a large amount of segment membranes is produced, the discharged water contains a large amount of acid residues, alkali residues, and organic matters, with the COD value and the BOD value greatly exceeding the values required by environmental protection. At present, a method comprising pH adjustment followed by pectin precipitation, and pressing followed by aeration treatment is mostly adopted. The method has a high treatment cost, and the pectin press residue cannot be directly stacked. The canned citrus processing enterprises consume a large amount of water. According to the Canning Industry Manual, it takes 60 tons of water to produce 1 ton of canned citrus fruit segments in syrup. After technical transformation, most enterprises consume more than 30 tons of water per ton of canned citrus segments in syrup, the discharge quantity is large and the treatment cost is high.

The acid and alkali treatment discharge water is rich in prebiotics such as pectin, flavonoids, oligosaccharides, other fibers, etc., has a function of reversing the disorder of intestinal flora, and can produce a high-value prebiotic product after being fully recycled, while solving the discharge problem of acid and alkali treatment water, thereby generating enormous social and environmental benefits. The citrus fruit segments are all wrapped in citrus peels, and have no risks of pesticide residues, chemical pollution and the like. Soaking treatment of the citrus fruit segments with acid solution and alkaline solution avoids the risk of microbial contamination. Therefore, the obtained acid and alkali treatment water has high safety for recycling.

SUMMARY

An object of the present disclosure is to provide a method for rapidly preparing a citrus-derived complex prebiotic agent by using discharged water from acid and alkali segment membrane removal treatment in the processing of canned citrus fruits as a raw material. A key procedure of the method is to sequentially treat citrus fruit segments by using an acid solution such as citric acid and an alkali solution such as potassium hydroxide or sodium hydroxide to remove segment membranes thereof. The alkali-treated water is adjusted with acid-treated water or acid to be weakly acidic to basic to obtain a complex prebiotic functional agent rich in pectin, flavonoids, oligosaccharides and other fibers. According to the present disclosure, the complex prebiotic product with an intestinal probiotic function is obtained from a citrus fruit processing water at a lower cost by using a simple operation unit, which is expected to obtain a certain economic benefit, supplements the comprehensive utilization process of citrus fruit processing while solving the discharge problem of citrus fruit processing water at the same time, and generates certain social benefits.

The object of the present disclosure is achieved by the following technical solution: a method for preparing a citrus-derived complex prebiotic agent, comprising the following steps:

(4) subjecting segments of a citrus fruit to soaking treatment with a certain volume of an acid solution having a concentration greater than 0.05 g/100 mL, until membranes of the segments become gel-like, and filtering the segments to obtain acid-treated water;

(5) transferring the acid-treated segments to a certain volume of an alkali solution having a concentration greater than 0.1 g/100 mL, subjecting the acid-treated segments to soaking treatment with the alkali solution until the membranes of the segments are dissolved, and performing filtering to obtain alkali-treated water; and (6) adjusting pH of the alkali-treated water with the acid-treated water or an acid to 4-7, and performing filtering to obtain a complex prebiotic agent.

Further, the citrus fruit is selected from citrus plants, and comprises, but is not limited to, Citrus reticulate Blanco, pomelo, orange, grapefruit, and lemon.

Further, the acid used comprises, but is not limited to, hydrochloric acid, citric acid, oxalic acid, tartaric acid, malic acid, and lactic acid, of food grade.

Further, a ratio of the citrus segments to the acid solution is 1 g:1 mL to 1 g:5 mL.

The method according to claim 1 is characterized in that the concentration of the acid solution is 0.4 to 0.8 g/100 mL, and the treatment is performed at a temperature of 5 to 80° C. for 20 min to 40 min.

Further, the alkali used includes, but is not limited to, NaOH, $Na_2CO_3$, KOH, $K_2CO_3$, $Mg(OH)_2$, and $Ca(OH)_2$, of food grade.

Further, a ratio of the segments to the alkali solution is 1 g:1 mL to 1 g:5 mL.

Further, the concentration of the alkali solution used is 0.4 to 0.8 g/100 mL, and the treatment is performed at a temperature of 5 to 80° C. for 10 min to 15 min.

Use of the above agent in manufacture of prebiotic oral liquids, prebiotic powders, and health care products for reversing intestinal flora disorders caused by antibiotics.

A preparing method of complex prebiotic powders includes: spray-drying the citrus-derived complex prebiotic agent to obtain the citrus-derived complex prebiotic powder.

The present disclosure has the beneficial effects that: the complex prebiotic product having the intestinal probiotic function is obtained from citrus processing water at a lower cost by using a simple operation unit. The present disclosure has the following characteristics:

(1) The product is directly obtained by a simple operation unit without carrying out a special desalination process;

(2) The raw material of the product is citrus processing water, and the product has a low cost and good safety;

(3) The processing procedure supplements a comprehensive utilization of citrus fruit processing wastewater, the COD value of discharged water is greatly reduced, and very good social benefits are provided;

(4) A complex prebiotic product is provided, the product contains various prebiotics such as pectin, flavonoids, oligosaccharides and other fibers, and synergistic effects of the various components can effectively reverse intestinal flora disorders caused by antibiotics. In addition, the pectin component in the product has the functions of reducing the serum cholesterol content, controlling the blood sugar content, preventing allergy, preventing occurrence and metastasis of cancers, and helping to remove heavy metal elements in the body and the like, the flavonoids have hypolipidemic, antiallergic, anticancer, antiviral, anti-inflammatory, antibacterial, and capillary strengthening functions, the oligosaccharides have functions of relaxing bowels, reducing the serum cholesterol content and the like, and the other fibers have functions of controlling body weight, preventing intestinal cancer and constipation, reducing blood fat, controlling blood sugar and the like.

DESCRIPTION OF EMBODIMENTS

Example 1

In the present example, citrus fruits were put in boiling water to be treated for 0.5 min, so that peels and piths detached from segments of the citrus fruits more easily. The peels and piths were removed from the citrus fruits treated with the boiling water while they were still warm. The citrus fruit segments were treated with a citric acid solution having a concentration of 0.4 g/100 mL according to a ratio of citrus fruit segments to acid water of 1 g:1 mL at a temperature of 20° C. for 20 min. The solution was continuously stirred during the treatment to ensure sufficient contact between the acid solution and the citrus fruit segments. However, it should be noted that the stirring should not be too intense, so as not to break the citrus fruit segments.

The acid-treated citrus fruit segments were respectively added to a sodium carbonate solution having a concentration of 0.4 g/100 mL to be treated according to a ratio of citrus fruit segments to alkali water of 1 g:1 mL at a temperature of 30° C. for 10 min. The solution should be continuously stirred during the treatment to ensure sufficient contact between the alkali solution and the citrus fruit segments. However, it should be noted that the stirring should not be too intense, so as not to break the citrus fruit segments.

The alkali-treated water was adjusted with the acid-treated water until the pH of the mixed liquid was 7 to obtain a complex prebiotic oral liquid. Under such treatment conditions, the precipitate in the oral liquid is less, and the citrus fruit segments obtained after the treatment have good integrity.

The pectin content, flavonoid content and oligosaccharide content of the obtained complex prebiotic oral liquid were determined:

Pectin Content 150 mL of the oral liquid was taken, and 95% ethanol was added to the sample according to a volume ratio of ethanol to sample of 1:1 to precipitate at room temperature for 2 h. The sample ethanol precipitation solution was transferred to a 300-mesh filter bag to be filtered, residues were washed twice with 15 mL of 95% ethanol, and filtered as above. The filter residues were transferred to a crucible with a spatula, and the crucible was dried together with the filter residues at a temperature of 50° C. for 6 h. After the filter residues were dried to constant weight, the mass thereof was determined. The pectin content of the oral liquid was determined to be 1144.00 μg/mL.

Flavonoid Content

Figure 1:
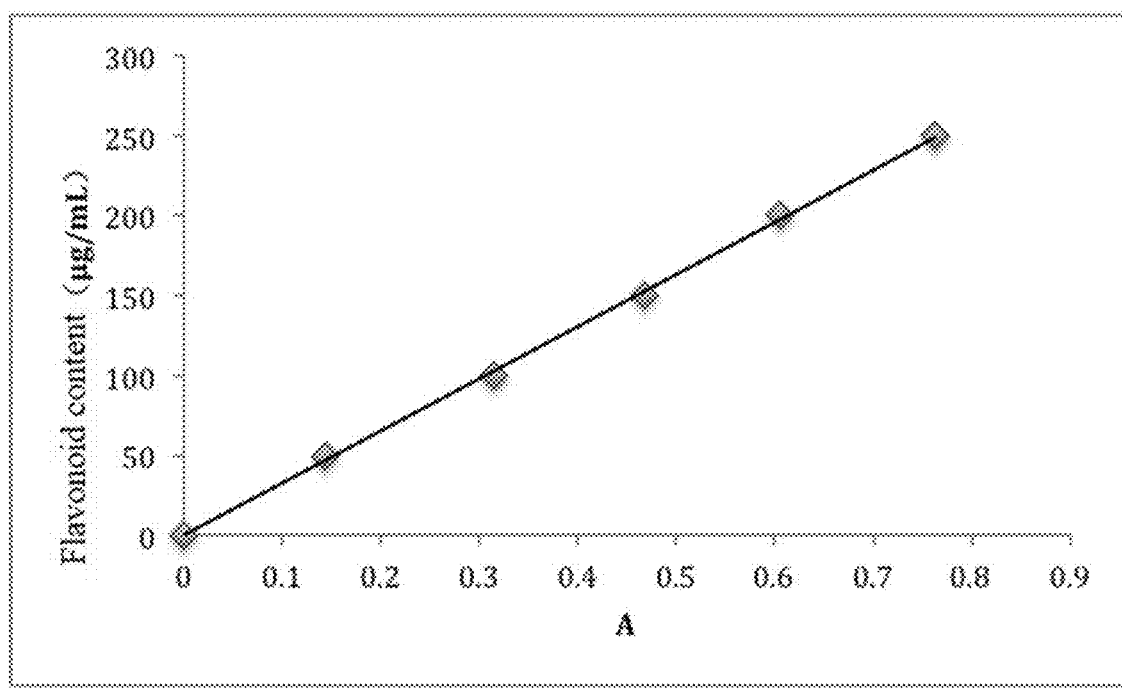
FIG. 1 is a standard curve of flavonoid content.

The flavonoid content analysis was based on a sodium nitrite method. 25 mg of hesperidin was taken, dissolved in a 0.4 g/L sodium hydroxide solution, and diluted to 50 mL. Standard sample solutions having concentrations of 0, 50, 100, 150, 200, and 250 μg/mL were sequentially prepared. 1 mL of each standard sample solution was taken, and added with 4 mL of a 0.4 g/L sodium hydroxide solution to obtain 5 mL of a reaction liquid. The reaction liquid was put in a 80° C. water bath, added with 0.6 mL of a 5% sodium nitrite solution to be evenly mixed, added with 0.6 mL of a 10% sodium nitrate solution to be evenly mixed, added with 4 mL of a 1 mol/L 80° C. sodium hydroxide solution, and put in a 80° C. water bath for 10 min, after cooling, a blank solution prepared by using 1 mL of the above 0.4 g/L sodium hydroxide solution was used as a reference, and the absorbance thereof was determined at a wavelength of 356 nm. A standard curve was drawn by using the hesperidin concentration (m/mL) as the abscissa and the absorbance as the ordinate, as shown in FIG. 1, the regression equation, $y=326.55x+0.096$, $R^2=0.999$, was obtained by calculation. 1 mL of the sample was taken, the absorbance value thereof was determined by the same method, and the flavonoid content thereof was calculated by using the standard curve. The flavonoid content of the oral liquid was determined to be 237.66 μg/mL.

Oligosaccharide Content

Figure 2:
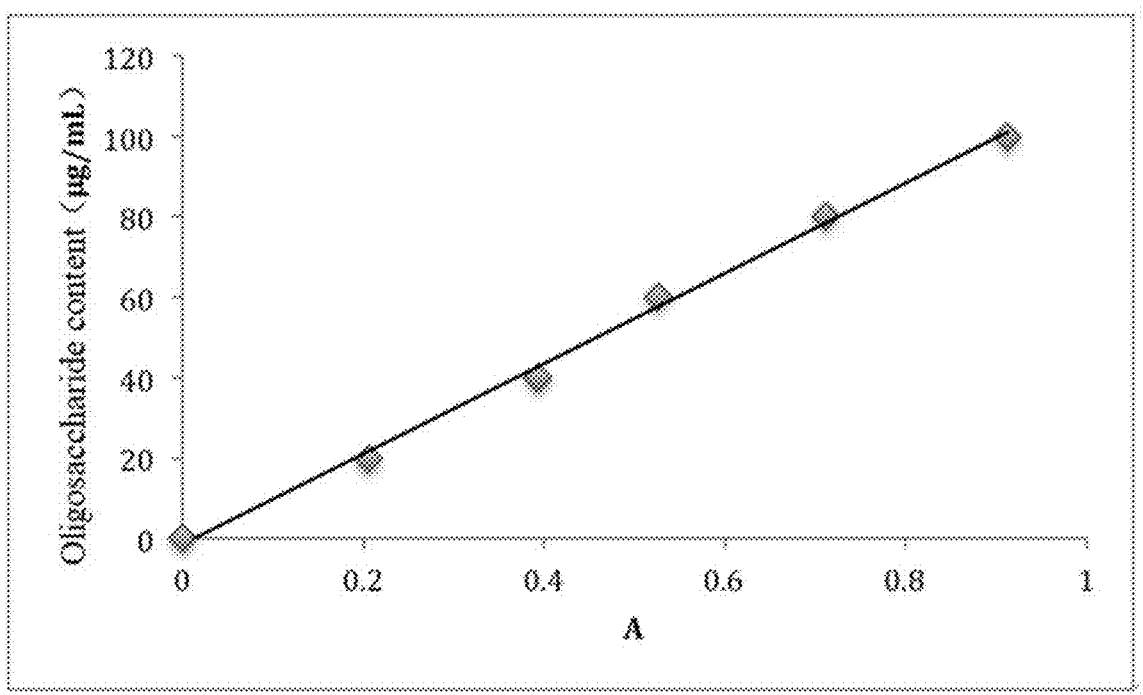
FIG. 2 is a standard curve of oligosaccharide content.
Figure 3:
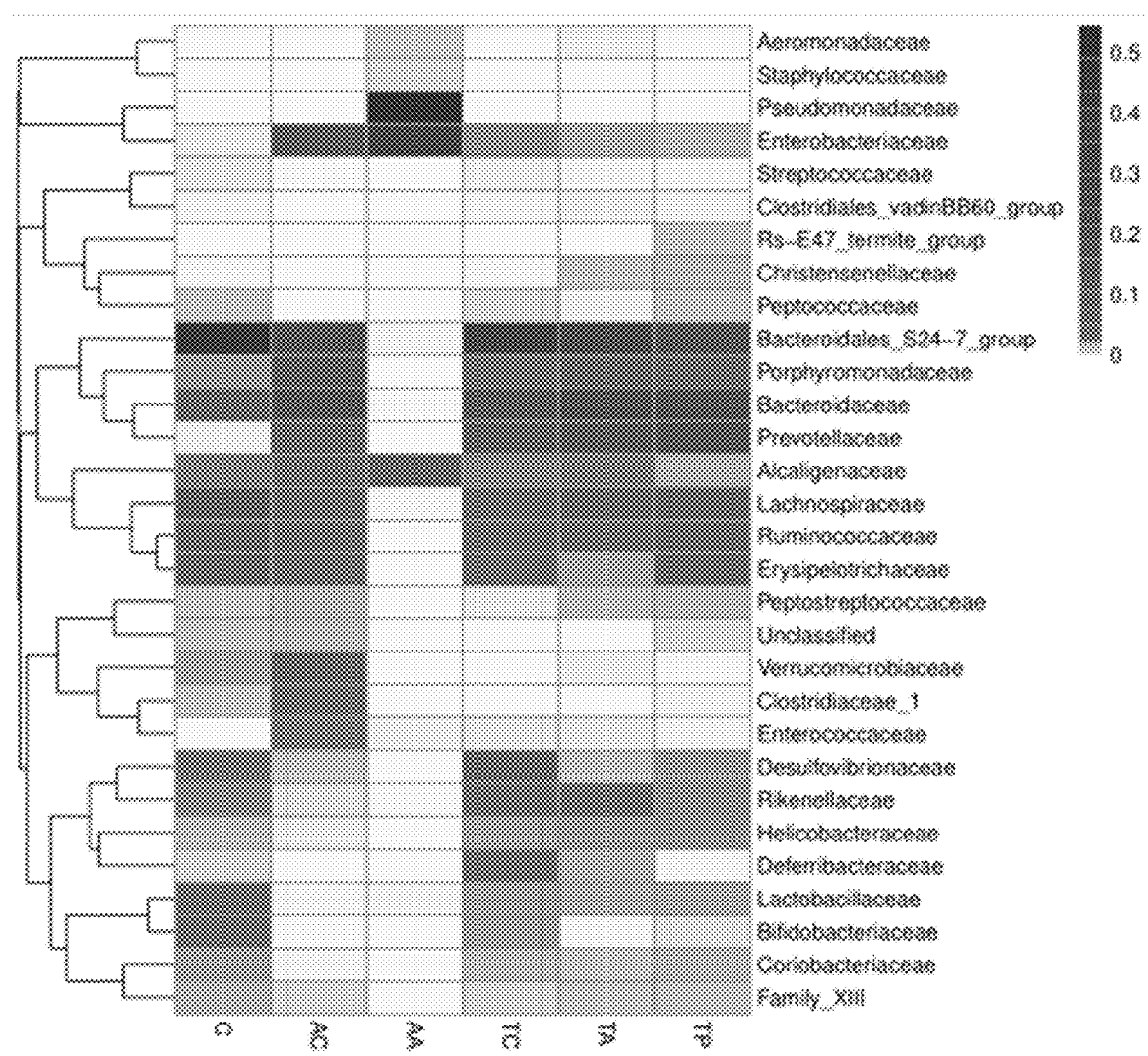
FIG. 3 is a bacteria distribution map at a genus level, where C: feces before the experiment begins, AC: control feces 1 week after administrating water, AA: feces in a model group one week after administrating antibiotics, TC: feces after 2 weeks in a control group, TA: feces after 2 weeks in the model group, and TP: feces 2 weeks after intragastrically administrating a powder in the model group.

The oligosaccharide analysis was based on a phenol-sulfuric acid method. Since after macromolecular polysaccharides were removed from the oral liquid by alcohol precipitation, the saccharides contained in the sample were oligosaccharides, the product oligosaccharides can be measured by the method. 20 mg of glucose was taken, and dissolved in water and diluted to 100 mL. Standard sample solutions having concentrations of 0, 20, 40, 60, 80, and 100 μg/mL were sequentially prepared. 2 mL of each standard sample solution was taken, added with 1 mL of a 5% phenol solution (newly prepared) to be evenly mixed, and added with 8 mL of concentrated sulfuric acid to be evenly mixed immediately to be kept warm in a boiling water bath for 20 min, taken out, and cooled in a cold water bath. A blank solution prepared by using 2 mL of the above water was used as a reference, and the absorbance of each solution was measured at a wavelength of 490 nm. A standard curve was drawn by using the glucose diluent concentration (μg/mL) as the abscissa and the absorbance as the ordinate, as shown in FIG. 2, the regression equation, $y=112.42x-1.5083$, $R^2=0.999$, was obtained by calculation. 2 mL of the sample diluent was taken, the absorbance value thereof was measured by the same method, and the oligosaccharide content thereof was calculated by using the standard curve. The oligosaccharide content of the oral liquid was determined to be 282.37 µg/mL.

Example 2

In the present example, the citrus fruits were put in boiling water to be treated for 0.5 min, so that the peels and piths detached more easily from the segments of the citruses. The citrus peels and piths were removed from the citrus fruits treated with the boiling water while they were still warm. The citrus fruit segments were treated with a citric acid solution having a concentration of 0.8 g/100 mL according to a ratio of citrus fruit segments to acid water of 1 g:5 mL at a temperature of 30° C. for 40 min. The solution was continuously stirred during the treatment to ensure sufficient contact between the acid solution and the citrus fruit segments. However, it should be noted that the stirring should not be too intense, so as not to break the citrus fruit segments.

The acid-treated citrus fruit segments were respectively added to a sodium carbonate solution having a concentration of 0.8 g/100 mL to be treated according to a ratio of citrus fruit segments to alkali water of 1 g:5 mL at a temperature of 40° C. for 15 min. The solution should be continuously stirred during the treatment to ensure sufficient contact between the alkali solution and the citrus fruit segments. However, it should be noted that the stirring should not be too intense, so as not to break the citrus fruit segments.

The alkali-treated water was adjusted with the acid-treated water until the pH of a mixed liquid was 7 to obtain a complex prebiotic oral liquid. Under the treatment conditions, the precipitate in the oral liquid is less, and the citrus fruit segments obtained after the treatment have good integrity.

The pectin content, flavonoid content, and oligosaccharide content thereof were determined according to the determination methods in Example 1. The determined results were as follows: pectin content: 475.00 µg/mL, flavonoid content: 71.24 µg/mL, and oligosaccharide content: 205.10 µg/mL.

Example 3

In the present example, the citrus fruits were put in boiling water to be treated for 0.5 min, so that the peels and piths detached more easily from the segments of the citrus fruits. The citrus peels and piths were removed from the citrus fruits treated with the boiling water while they were still warm. The citrus fruit segments were treated with a citric acid solution having a concentration of 0.05 g/100 mL according to a ratio of citrus fruit segments to acid water of 1 g:1 mL at a temperature of 5° C. for 10 min. The solution was continuously stirred during the treatment to ensure sufficient contact between the acid solution and the citrus fruit segments. However, it should be noted that the stirring should not be too intense, so as not to break the citrus fruit segments. The acid-treated citrus fruit segments were respectively added to a sodium carbonate solution having a concentration of 0.1 g/100 mL to be treated according to a ratio of citrus fruit segments to alkali water of 1 g:1.5 mL at a temperature of 5° C. for 5 min. The solution should be continuously stirred during the treatment to ensure sufficient contact between the alkali solution and the citrus fruit segments. However, it should be noted that the stirring should not be too intense, so as not to break the citrus fruit segments. The alkali-treated water was adjusted with the acid-treated water until the pH of a mixed liquid was 7 to obtain a complex prebiotic oral liquid. Under the treatment conditions, the precipitate in the oral liquid is less, and the citrus fruit segments obtained after treatment have good integrity.

The pectin content, flavonoid content, and oligosaccharide content thereof were determined according to the determination methods in Example 1. The determined results were as follows: pectin content: 972.00 µg/mL, flavonoid content: 223.89 µg/mL, and oligosaccharide content: 698.43 µg/mL.

Example 4

In the present example, the citrus fruits were put in boiling water to be treated for 0.5 min, so that the peels and piths detached more easily from the segments of the citrus fruits. The citrus peels and piths were removed from the citrus fruits treated with the boiling water while they were still warm. The citrus fruit segments were treated with a citric acid solution having a concentration of 1 g/100 mL according to a ratio of citrus fruit segments to acid water of 1 g:5 mL at a temperature of 80° C. for 60 min. The solution was continuously stirred during the treatment to ensure sufficient contact between the acid solution and the citrus fruit segments. However, it should be noted that the stirring should not be too intense, so as not to break the citrus fruit segments. The acid-treated citrus fruit segments were respectively added to a sodium carbonate solution having a concentration of 1 g/100 mL to be treated according to a ratio of citrus fruit segments to alkali water of 1 g:1.5 mL at a temperature of 80° C. for 60 min. The solution should be continuously stirred during the treatment to ensure sufficient contact between the alkali solution and the citrus fruit segments. However, it should be noted that the stirring should not be too intense, so as not to break the citrus fruit segments. The alkali-treated water was adjusted with the acid-treated water until the pH of a mixed liquid was 7 to obtain a complex prebiotic oral liquid.

The pectin content, flavonoid content, and oligosaccharide content thereof were determined according to the determination methods in Example 1. The determined results were as follows: pectin content: 630.56 µg/mL, flavonoid content: 114.78 µg/mL, and oligosaccharide content: 476.78 µg/mL.

Example 5

In the present example, the citrus fruits were put in boiling water to be treated for 0.5 min, so that the peels and piths detached more easily from the segments of the citrus fruits. The citrus peels and piths were removed from the citrus fruits treated with the boiling water while they were still warm. The citrus fruit segments were treated with a citric acid solution having a concentration of 0.6 g/100 mL according to a ratio of citrus fruit segments to acid water of 1 g:1.5 mL at a temperature of 28° C. for 30 min. The solution was continuously stirred during the treatment to ensure sufficient contact between the acid solution and the citrus fruit segments. However, it should be noted that the stirring should not be too intense, so as not to break the citrus fruit segments. The acid-treated citrus fruit segments were respectively added to a sodium carbonate solution having a concentration of 0.6 g/100 mL to be treated according to a ratio of citrus fruit segments to alkali water of 1 g:1.5 mL at a temperature of 32° C. for 10 min. The solution should be continuously stirred during the treatment to ensure sufficient contact between the alkali solution and the citrus fruit segments. However, it should be noted that the stirring should not be too intense, so as not to break the citrus fruit segments. The alkali-treated water was adjusted with the acid-treated water until the pH of a mixed liquid was 7 to obtain a complex prebiotic oral liquid.

The pectin content, flavonoid content, and oligosaccharide content thereof were determined according to the determination methods in Example 1. The determined results were as follows: pectin content: 1125.47 µg/mL, flavonoid content: 204.39 µg/mL, and oligosaccharide content: 475.21 µg/mL.

Example 6

In the present example, the citrus fruits were put in boiling water to be treated for 0.5 min, so that the peels and piths detached more easily from the segments of the citrus fruits. The citrus peels and piths were removed from the citrus fruits treated with the boiling water while they were still warm. The citrus segments were treated with a citric acid solution having a concentration of 0.6 g/100 mL according to a ratio of citrus segments to acid water of 1 g:1.5 mL at a temperature of 28° C. for 30 min. The solution was continuously stirred during the treatment to ensure sufficient contact between the acid solution and the citrus segments. However, it should be noted that the stirring should not be too intense, so as not to break the citrus fruit segments. The acid-treated citrus fruit segments were respectively added to a sodium carbonate solution having a concentration of 0.6 g/100 mL to be treated according to a ratio of citrus fruit segments to alkali water of 1 g:1.5 mL at a temperature of 32° C. for 10 min. The solution should be continuously stirred during the treatment to ensure sufficient contact between the alkali solution and the citrus fruit segments. However, it should be noted that the stirring should not be too intense, so as not to break the citrus fruit segments. The alkali-treated water was adjusted with the acid-treated water until the pH of a mixed liquid was 7, and the mixed liquid was spray-dried to obtain a complex prebiotic powder. The product contains 40-60% of pectin, 10-20% of flavonoid, and 30-40% of oligosaccharide.

Example 7

In the present example, the citrus fruits were put in boiling water to be treated for 0.5 min, so that the peels and piths detached more easily from the segments of the citrus fruits. The citrus peels and piths were removed from the citrus fruits treated with the boiling water while they were still warm. The citrus fruit segments were treated with a citric acid solution having a concentration of 0.6 g/100 mL according to a ratio of citrus fruit segments to acid water of 1 g:1.5 mL at a temperature of 28° C. for 30 min. The solution was continuously stirred during the treatment to ensure sufficient contact between the acid solution and the citrus fruit segments. However, it should be noted that the stirring should not be too intense, so as not to break the citrus fruit segments. The acid-treated citrus fruit segments were respectively added to a sodium carbonate solution having a concentration of 0.6 g/100 mL to be treated according to a ratio of citrus fruit segments to alkali water of 1 g:1.5 mL at a temperature of 32° C. for 10 min. The solution should be continuously stirred during the treatment to ensure sufficient contact between the alkali solution and the citrus fruit segments. However, it should be noted that the stirring should not be too intense, so as not to break the citrus fruit segments. The alkali-treated water was adjusted with the acid-treated water until the pH of a mixed liquid was 7, and the mixed liquid was freeze-dried to obtain a complex prebiotic powder.

The powder has the function of reversing the intestinal flora disorder. An intestinal flora imbalance mouse model was prepared by intragastrically administrating broad-spectrum antibiotics, and a normal control group and a powder intervention group were also set up at the same time. 16SRNA sequencing was performed on the test mouse flora, and OTU analysis, species analysis, principal component analysis, difference significance analysis of community structures between groups and the like were performed. The intestinal flora diversity of the mice in the powder intervention group was increased significantly and was similar to that in the normal control group, which indicates that the powder intervention can reverse the mice's intestinal flora disorder caused by the antibiotics. The relative abundance of beneficial bacteria such as Bifidobacteria and Bacteroides of mice in the powder intervention group was also significantly increased, while the abundance of harmful bacteria such as Paeruginosa (Pseudomonas aeruginosa) and Escherichia-Shigella (Escherichia coli Shigella) was significantly reduced.

What is claimed is:

1. A method for preparing a citrus-derived complex prebiotic composition, comprising the following steps:
    (1) subjecting segments of a citrus fruit to a soaking treatment with a certain volume of an acid and water solution having a concentration greater than 0.05 g/100 mL, until membranes of the segments of the citrus fruit become gel-like, and filtering the segments of the citrus fruit to obtain an acid-treated water;
    (2) transferring the acid-treated segments of the citrus fruit to a certain volume of an alkali and water solution having a concentration greater than 0.1 g/100 mL, subjecting the acid-treated segments of the citrus fruit to soaking treatment with the alkali and water solution until the membranes of the segments of the citrus fruit are dissolved, and performing filtering to obtain an alkali-treated water; and
    (3) adjusting the pH of the alkali-treated water with the acid-treated water to a pH of 4-7, and performing filtering to obtain a complex prebiotic composition wherein the alkali is selected from the group consisting of NaOH, $Na_2CO_3$, KOH, $K_2CO_3$, $Mg(OH)_2$, and $Ca(OH)_2$, the acid is selected from the group consisting of hydrochloric acid, citric acid, oxalic acid, tartaric acid, malic acid, and lactic acid, and the citrus fruit is selected from the group consisting of Citrus reticulate Blanco, pomelo, orange, grapefruit, and lemon.

2. The method of claim 1, wherein the ratio of the citrus segments to the acid and water solution is 1 g:1 mL to 1 g:5 mL.

3. The method of claim 1, wherein the concentration of the acid and water solution is 0.4 to 0.8 g/100 mL, and the treatment is performed at a temperature of 5° C. to 80° C. for 20 minutes to 40 minutes.

4. The method of claim 1, wherein the ratio of the citrus segments to the alkali and water solution is 1 g: 1 mL to 1 g:5 mL.

5. The method of claim 1, wherein the concentration of the alkali and water solution used is 0.4 to 0.8 g/100 mL, and the treatment is performed at a temperature of 5° C. to 80° C. for 10 minutes to 15 minutes.

\* \* \* \* \*